United States Patent
Shultz et al.

(10) Patent No.: US 6,242,235 B1
(45) Date of Patent: Jun. 5, 2001

(54) POLYMERASE STABILIZATION BY POLYETHOXYLATED AMINE SURFACTANTS

(75) Inventors: John W. Shultz, Verona; Fen Huang, Madison, both of WI (US)

(73) Assignee: Promega Corp., Madison, WI (US)

( * ) Notice: Subject to any disclaimer, the term of this patent is extended or adjusted under 35 U.S.C. 154(b) by 0 days.

(21) Appl. No.: 09/338,174

(22) Filed: Jun. 22, 1999

Related U.S. Application Data
(60) Provisional application No. 60/090,539, filed on Jun. 24, 1998.

(51) Int. Cl.$^7$ ............................... C12N 9/12; C12N 9/96
(52) U.S. Cl. ........................................... 435/194; 435/188
(58) Field of Search ..................... 435/188, 194

(56) References Cited

U.S. PATENT DOCUMENTS

| | | | |
|---|---|---|---|
| Re. 34,157 | * 1/1993 | Sramek | 424/47 |
| 4,303,752 | * 12/1981 | Kolehmainen et al. | 435/8 |
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |
| 5,210,036 | 5/1993 | Comb et al. | 435/194 |
| 5,352,600 | 10/1994 | Gelfand et al. | 435/194 |

FOREIGN PATENT DOCUMENTS

776970 A1    6/1997  (EP) .

OTHER PUBLICATIONS

Jones, *Surface Activity of Proteins*, S. Magdassi (ed.), Marcel Dekker, Inc., New York, pp. 237–284 [1996].
Deutscher (ed.), *Methods in Enzymology–Guide to Protein Purification*, Academic Press Limited, London [1990]p. 279.
Wu et al., Biochemistry, 14: 789–95 [1975].
Nozaki et al., J. Biol. Chem., 249: 4452–59 [1974].
Kacian et al., Proc. Natl. Acad. Sci. USA 69: 3038 [1972].
Chamberlin et al., Natre 228: 227 [1970].
Wu and Wallace, Genomics 4: 560 [1989].
Steinhardt and Reynolds (eds.), *Multiple Equilibrium and Proteins*, Academic Press, New York, pp. 234–350 [1969].
Markus et al., J. Biol. Chem., 239: 3687 [1964].
Wilson et al., "Studies on DNA Synthesis in Mrine Myeloma: II. Activation of Latent RNA–Dependent DNA Polymerase Activity in Membrane Fractions," Biochem. Biophys. Res. Comm, 49 (4): 1093 (1972).
Schmid, "Stabilized Soluble Enzymes," Advances in Biochemical Eng., 12:41–118 (1979).
Daniel et al., "The Denaturation and Degradation of Stable Enzymes at High Temperatures," Biochem. J., 317: 1–11 (1996).
Anfinsen, "The Formation and Stabilization of Protein Structure," Biochem. J., 128:737–749 (1972).

Aoki and Hiramatsu, "The interaction of Bovine Plasma Albumin with Cationic Detergents at pH 9," Analytical Biochemistry 60:213–225 (1974).
Yokoyama et al., "Stabilization of Crystalline Acid Carboxypeptidase from *Penicillium janthinellum* by nonionic surfactants, and inhibition of enzyme activity by anionic compounds," Agric. Biol. Chem., 41(8): 1379–1383 (1977).
Klibanov, "Stabilization of Enzymes Against Thermal Inactivation," Advances in Applied Microbiology, 26: 1–25 (1983).
Klibanov, "Approaches to Enzyme Stabilization," Biochemical Society Transactions, 11: 19–20 (1983).
Gianfreda and Scarfi, "Enzyme Stabilization: State of the Art," Molecular and Cellular Biochemistry, 100: 97–128 (1991).
Kraut, "How do Enzymes Work," Science, 242:533 (1988).
Ray et al., "Binding of Large Organic Anions and Neutral Molecules by Native Bovne Serum Albumin," Biochemistry, 5(8):2606 (1966).
Nelson "The Binding of Detergents to Proteins," J. Biol. Chem. 246:3895–3901 (1971).
Takagi et al., "Binding Isotherms of Sodium Dodecyl Sulfate to Protein Polypeptides with Special Reference to SDS–Polyacrylamide Gel Electrophoresis," J. Biochem., 77: 939–947 (1975).
Reynolds and Tanford, "Binding of Dodecyl Sulfate to Proteins at High Binding Ratios. Possible Implications of the State of Proteins in Biological Membranes," PNAS, 66(3): 1002–1003 (1970).
Berfeld et al., "Reversible Dissociation of Enzymes at High Dilutions and their Inhibition by Polyanions," Archives Biochemistry Biophysics 111:31–38 (1965).
Markovic–Housley and Garavito, "Effect of Temperature and Low pH on Structure and Stability of Matrix Porin in Micellular Detergent Solutions," Biochemica et Biophsica Acta 869: 158–170 (1986).
Cacciapuoti et al., "Purification and Characterization of Extremely Thermophilic and Thermostable 5'–methylioadenosine Phosphorylase from the Archaeon *Sulfolobus solfataricus*, " J. Biol. Chem. 269:24762–24769 (1994).
Waehneldt, "Sodium Dodecyl Sulfate in Protein Chemistry," Biosystems 6:176–187 (1975).
Reynolds et al., "The Binding of Divers Detergent Anions to Bovine Serum Albumin," Biochemistry 6(3):937 (1967).
Reynolds et al., "The Binding of Some Long–Chain Fatty Acid Anions and Alcohols by Bovine Serum Albumin," Biochemistry 7(4):1357 (1968).

(List continued on next page.)

*Primary Examiner*—Jon P. Weber

(57) ABSTRACT

The present invention provides methods and compositions for protein stabilization, particularly the stabilization of polymerases in aqueous solutions with cationic surfactants. The present invention further provides cationic surfactants, including polyethoxylated amines, that stabilize thermostable and thermolabile enzymes in solution. These surfactants stabilize the activity of various enzymes, including thermostable DNA polymerases, thermolabile DNA polymerases and reverse transcriptases.

23 Claims, No Drawings

OTHER PUBLICATIONS

Jones et al., "The Interaction Between Bovine Serum Albumin and Surfactants," Biochem. J. 147:229–234 (1975).

Callahan et al., "Sphingomyelinases in Human Tissues. IV. Purification of Sphingomyelinase from Human Placenta and Effect of Triton X–100," Can. J. Biochem. 56:885 (1978).

Takeda and Hizukuri, "Effect of Triton X–100 on Sweet Potato β–Amylase," Biochimica et Biophysica Acta 268:175–183 (1972).

Stubbs and Litman, "Effect of Alterations in the Amphipathic Microenviornment on the Conformational Stability of Bovine Opsin. 1. Mechanism of Solubilization of Disk Membranes by the Nonionic Detergent, Octyl Glucoside," Biochemisty 17: 215 (1978).

Makino et al., "The Binding of Deoxycholate and Triton X–100 to Proteins," J. Biol. Chem. 248: 4926–4932.

Komori et al., "The Effect of Nonionic Detergents on the Activity and/or Stability of Rat Brain Nitric Oxide Synthase," Archives of Biochemistry and Biophysics, 307: 311–315.

* cited by examiner

POLYMERASE STABILIZATION BY POLYETHOXYLATED AMINE SURFACTANTS

This invention claims the benefit of U.S. Provisional Application Ser. No. 60/090,539 filed on Jun. 24, 1998.

FIELD OF THE INVENTION

The present invention relates to protein stabilization, particularly the stabilization of polymerases in aqueous solutions containing cationic surfactants.

BACKGROUND OF THE INVENTION

Stabilization of enzymes is necessary for the long term storage and utilization in many biochemical and biotechnological processes. Enzymes have been isolated from thermophilic organisms which are stable to denaturation by heat. However, even these highly thermostable enzymes may be inactivated by chemical agents, proteases, or environmental modifications. The utilization of thermostable and other enzymes often requires the concomitant use of denaturing conditions including highly elevated temperatures, aqueous environments with sub-optimal concentrations of cofactors and substrates, and a pH that is suboptimal for maximum enzyme stability.

Many stabilization techniques are known. These techniques include immobilization of the enzyme on solid substrates, chemical modification of the enzyme, genetic engineering of the enzyme and the addition of stabilizing additives. Surfactants are one group of additives that have been shown to stabilize enzymes. Surfactants are surface active compounds that stabilize the interface between the active form of the enzyme, and the liquid environment in which they are contained.

For example, non-ionic detergents have been variously shown to increase the solution stability of various proteins with enzymatic activity (e.g., cAMP-dependent protein kinase, tyrosine hydroxylase, nitric oxide synthase, tryptophan hydroxylase and a sweet potato beta-amylase). Additionally, non-ionic detergents such as TRITON X-100 and Tween 20 have been shown to stabilize the activity of DNA polymerases (See, e.g., Biochem., 14: 789–95 [1975]). European Patent Application 776,970 A1, incorporated herein by reference, discloses the use of non-ionic detergents including polyoxyethylated sorbitan monolaurate (Tween 20) and ethoxylated alky phenol (NP-40) to stabilize the activity of Taq thermostable DNA polymerase.

Low concentrations of the anionic detergent sodium dodecyl sulfate (SDS) have been shown to stabilize enzyme activity. However, due to the possibility of cooperative binding if the optimal concentration of SDS is exceeded in solution, the use of SDS in protein stabilization is limited. It is known, however, that many cationic detergents bind less strongly to proteins than strong anionic detergents such as SDS (See e.g., Nozaki et.al., J. Biol. Chem., 249:4452–59 [1974]). Furthermore, most proteins have fewer cationic binding sites than anionic binding sites.

The utility of enzymes such as DNA polymerases often is limited by the stability of the polymerase in solution. Thus, there is need for additives which improve the stability of enzymes in solution, particularly those additives which improve stability as well as avoid the drawbacks of currently used surfactants.

SUMMARY OF THE INVENTION

The present invention relates to protein stabilization, particularly the stabilization of polymerases in aqueous solutions with cationic surfactants.

In some embodiments, the present invention provides a composition comprising a mixture of a protein having enzymatic activity and a cationic surfactant. The present invention is not limited to any particular enzyme. Indeed, the stabilization of a variety of enzymes is contemplated. In some preferred embodiments, the protein is a polymerase (e.g., E. coli DNA polymerase I, Taq polymerase, Tne polymerase, Tth polymerase, T4 DNA polymerase, RNA polymerase II, SP6 RNA polymerase, T7 RNA polymerase, AMV reverse transcriptase, MMLV reverse transcriptase, etc.). In other embodiments, the enzyme is preferably a kinase, phosphorylase, or phosphatase (e.g., calf intestinal phosphatase).

Likewise, the present invention is not limited to a particular cationic surfactant. Indeed, a variety of cationic surfactants are contemplated. In some embodiments, the cationic surfactant has a Hydrophile-Lipophile Balance (HLB) index number of about 10 to 17. In some preferred embodiments, the cationic surfactant has a HLB index number of about 11 to 16. In other embodiments, the cationic surfactant is a polyethoxylated amine. In some particularly preferred embodiments, the polyethoxylated amine has the following structure:

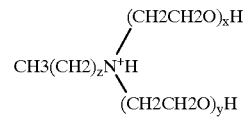

In some embodiments, z is an integer from about 15 to 20, most preferably 18. In other embodiments, x+y has an average value of about 5 to 15 so that the HLB index number is from about 11 to 16. In some preferred embodiments, x+y has an average value of 5 or 15. In some embodiments, the nitrogen may be substituted with a phosphorous, sulphur or arsenic radical. In still other embodiments, the cationic surfactant is present in the solution or mixture at a concentration of about 0.0005 to 1.0% by volume.

In some embodiments, the mixture or solution includes a buffering reagent. The present invention is not limited to a particular buffering reagent. Indeed, a variety of buffering reagents are contemplated. In some embodiments, the buffering reagent is preferably a MOPS, HEPES, or Tris buffer. In other embodiments, the concentration of the buffer in the solution is from about 10 mM to 70 mM. In some embodiments, the pH is from about 7.0 to 9.2.

In other embodiments, the solution or mixture includes a monovalent salt and/or a divalent salt. The present invention is not limited to any particular salt. Indeed, a variety of salts are contemplated, including, but not limited to, NaCl, KCl, $MgCl_2$, and $CaCl_2$. In some embodiments, the divalent cation is present at a concentration of about 0.1 to 10 mM. In other embodiments, the monovalent cation is present at a concentration of about 1 to 100 mM.

In still further embodiments, the solution or mixture includes a chelator and/or a reducing agent. The present invention is not limited to particular chelators and reducing agents. Indeed, a variety of chelators and reducing agents are contemplated. Preferred chelating agents include, but are not limited to, EDTA and EGTA. Preferred reducing agents include, but are not limited to, dithiothreitol and β-mercaptoethanol. In some embodiments, the chelating agent is present at a concentration of about 0.01 to 10 mM. In other embodiments, the reducing agent is present at a concentration of about 0.1 to 20 mM.

In some embodiments, the present invention provides methods for stabilizing proteins with enzymatic activity. In some embodiments, a protein with enzymatic activity (e.g., a polymerase, kinase, phosphatase, or phosphorylase) and a cationic surfactant are provided. In some preferred embodiments, the cationic surfactant has an HLB index number of from about 10 to 17. In particularly preferred embodiments, the cationic surfactant is a polyethoxylated amine, as described above. In other embodiments, the protein with enzymatic activity and cationic surfactant are combined so that the activity of the enzyme is stabilized as compared to the activity of the enzyme in the absence of the cationic surfactant.

Definitions

To facilitate an understanding of the invention, a number of terms are defined below.

As used herein, the term "enzyme" refers to molecules or molecule aggregates that are responsible for catalyzing chemical and biological reactions. Such molecules are typically proteins, but can also comprise short peptides, RNAs, ribozymes, antibodies, and other molecules. A molecule that catalyzes chemical and biological reactions is referred to as "having enzyme activity" or "having catalytic activity."

As used herein, the terms "stabilization," "stabilizing," and "stabilized," when used in reference to enzyme activity refer to the ability of a material to maintain, enhance, or otherwise inhibit the decline or loss of the activity of an enzyme, often as measured over time (i.e., in the presence of a stabilizer, an enzyme retains its activity for a longer time period than the enzyme in the absence of the stabilizer). "Stabilization of enzyme activity" also refers to the ability of a material to maintain the activity of an enzyme under suboptimal conditions of temperature or pH. As another example, "stabilizing enzyme activity" refers to the ability of a material to enhance enzyme activity under suboptimal conditions, as compared to activity in the absence of a "stabilizing" compound or material.

The term "polymerase" refers to an enzyme that synthesizes nucleic acid stands (e.g., RNA or DNA) from ribonucleoside triphosphates or deoxynucleoside triphosphates.

The term "polymerase activity" refers to the ability of an enzyme to synthesize nucleic acid stands (e.g., RNA or DNA) from ribonucleoside triphosphates or deoxynucleoside triphosphates. DNA polymerases synthesize DNA, while RNA polymerases synthesize RNA.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, *Surfactant Science and Technology,* VCH Publishers Inc., New York, pp. 231–245 [1992]), incorporated herein by reference. As used herein, the HLB Index Number of a surfactant is the HLB Index Number assigned to that surfactant in McCutcheon's Volume 1: Emulsifiers and Detergents North American Edition, 1996, incorporated herein by reference. The HLB Index Number ranges from 0 to about 70 or more for commercial surfactants. Hydrophilic surfactants with high solubility in water and solubilizing properties are at the high end of the scale, while surfactants with low solubility in water which are good solubilizers of water in oils are at the low end of the scale.

The term "polyethoxylated amine" refers to any surfactant which includes a hydrophobic alkyl side chain and one or more long-chain polyoxyethylene groups.

The terms "buffer" or "buffering agents" refer to materials which when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g. Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

The term "buffering solution" refers to a solution containing a buffering reagent.

The term "reaction buffer" refers to a buffering solution in which an enzymatic reaction is performed.

The term "storage buffer" refers to a buffering solution in which an enzyme is stored.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology,* Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that in preferred embodiments any probe used in the present invention will be labelled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, each of which is hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

GENERAL DESCRIPTION OF THE INVENTION

The present invention provides methods and compositions for protein stabilization, particularly the stabilization of polymerases in aqueous solutions with cationic surfactants. The activity of polymerases in solution, either in storage buffers or reaction buffers, may be stabilized by the addition of non-ionic surfactants. It is not intended that the present invention be limited to particular mechanism of action. Indeed, an understanding of the mechanisms involved in protein stabilization is not necessary to make and use the present invention. However, one theory regarding the mechanism of protein stabilization by surfactants is that the binding of a surfactant to a protein serves a cross-linking function that prevents unfolding or denaturation of the protein. In the case of non-ionic surfactants, the binding occurs at hydrophobic sites on the protein surface.

The mechanism of surfactant binding to proteins and denaturation by some ionic surfactants has been reviewed. (See e.g., Jones, in *Surface Activity of Proteins,* S. Magdassi (ed.), Marcel Dekker, Inc., New York, pp. 237–284 [1996]). The initial interaction between ionic surfactants and proteins is mediated by binding of the ionic head group to high-energy sites on the surface of the protein. The head group interactions with charged sites on the protein surface are electrostatic. Anionic surfactants bind to cationic sites (e.g., lysyl, histidyl, and arginyl residues). Cationic surfactants bind to anionic sites (e.g., glutamyl and aspartyl residues). The hydrophobic tail of the surfactant then interacts with hydrophobic regions on the protein surface.

Furthermore, many ionic detergents are known to cooperatively bind with proteins. Cooperative binding is characterized by an unfolding of the tertiary structure of the protein, allowing the binding of more surfactant molecules. The initial unfolding is believed to result from insertion of the hydrophobic tail of the surfactant into the hydrophobic interior of the protein. Cooperative binding generally results in complete denaturation of the protein, resulting in the loss of activity.

The binding affinity of surfactants for proteins is mediated by the nature of the head group, hydrophobic tail chain length, and the critical micelle concentration (CMC) of the surfactant. For anionic detergents, it has been demonstrated that for surfactants with a constant hydrophobic tail length, binding affinity decreases as the polar head group is varied in the order from $SO_4^- > SO_3^- > CO_2^- > OH$. Chain length is also a factor. For example, alkyl sulfates show binding with extensive unfolding when the alkyl chain-length is C12 (i.e., 12 carbons), and binding without extensive unfolding occurs when chain-length is less than C12. In contrast, for alkyl sulfinates, a C12 chain-length has been shown to be insufficient for cooperative binding.

Cooperative binding occurs at increasing surfactant concentrations. Whether or not cooperative binding occurs depends on the CMC of the surfactant. The CMC of the surfactant is the concentration at which the free surfactant molecules present in a solution aggregate to form micelles. For cooperative binding of a surfactant to a protein, the initial electrostatic binding occurs at concentrations of surfactant well below the CMC of the surfactant. Many strongly denaturing surfactants have relatively high CMCs. For surfactants with low CMCs, a surfactant will preferentially form micelles at relatively low concentrations of surfactant. Therefore, a surfactant concentration sufficient to cause denaturation of the protein cannot be reached in solution. Non-ionic detergents are limited by their CMCs and the free concentrations that they can attain, so that cooperative binding and denaturation cannot occur for any reasonable added excess of surfactant.

The binding of surfactants to proteins is studied by constructing binding isotherms. Isotherms are S-shaped curves produced by applying the average number of surfactant molecules per protein molecule plotted as a function of the logarithm of the free surfactant concentration. The binding isotherm has multiple regions. The first region consists of a relatively sharply increasing slope corresponding to specific binding of the surfactant to charge sites on the surface of the native protein or to hydrophobic regions. When these sites are saturated, a plateau-like region occurs. For surfactants which bind cooperatively with proteins, a third region of steep slope is apparent. This region generally occurs as free surfactant approaches a critical micelle concentration for the surfactant.

Mathematical models for binding-induced unfolding predict that the binding of small amounts of high affinity ions protect a protein from unfolding by other agents (See e.g., Steinhardt and Reynolds (eds.), *Multiple Equilibrium and Proteins,* Academic Press, New York, pp. 234–350 [1969]). Protection from unfolding is based on the electrostatic interaction between the charged head groups of some surfactants with charged residues on the surface of the protein (Markus et al., J. Biol. Chem., 239:3687 [1964]). Subsequent binding of the hydrophobic tail the hydrophobic areas on the protein then provides a non-covalent cross linking function.

The present invention provides surfactants which stabilize enzyme activity. In some embodiments, the ethoxylated alkyl amine cationic surfactants Tomah E-18-5 and Tomah E-18-15 (Tomah Prod Inc, Milton, Wis.) provided equal or superior stabilization of polymerases in solution compared to commonly used non-ionic surfactants such as Tween 20, TRITON X-100 and NP-40. In one assay, surfactant stabilization of the thermostable DNA polymerases isolated from *Thermus aquaticus* (Taq polymerase), *Thermus thermophilius* (Tth polymerase), and *Thermus flavus* (Tfl polymerase) was measured by the ability to catalyze the polymerase chain reaction (PCR). The amount of reaction product obtained was taken to be a measure of the stability of the enzyme used in the reaction. Superior results were observed when lower levels of Taq or Tth polymerase were used in conjunction with the cationic detergents. Amplification of the target DNA sequence was readily and reproducibly apparent in reactions containing as much as 50% less polymerase activity than was needed to amplify the target in the non-ionic surfactant control reactions. In another assay, the half-lives of Tth and Taq polymerase in buffers containing the cationic detergents were determined to be equal to or greater than their half-lives observed in buffers containing non-ionic surfactants.

In other embodiments of the present invention, cationic surfactants are also used to stabilize other enzymes, including, but not limited to T4 DNA polymerase, MMLV (Moloney Murine Leukemia Virus) reverse transcriptase, and AMV (Avian Myeloblastosis Virus) reverse transcriptase. In experiments to demonstrate the stabilization of these enzymes, polymerization reaction mixtures containing DNA or RNA templates were assembled using either the standard stabilizer BSA (bovine serum albumin) or the cationic surfactants. The activity of T4 polymerase and MMLV and AMV reverse transcriptase, as determined by incorporation of radioactive dNTPs into nucleic acid, was enhanced in the reaction buffers containing the cationic surfactants as compared to the reaction buffers containing BSA.

The cationic surfactants of the present invention are therefore useful in stabilizing both thermostable and thermolabile polymerases, including, but not limited to, Taq polymerase, Tth polymerase, Tfl polymerase, T4 DNA polymerase, AMV reverse transcriptase and MMLV reverse transcriptase. These cationic surfactants find use as stabilizers in either reaction buffers or storage buffers.

DETAILED DESCRIPTION OF THE INVENTION

A. Identification of Surfactants Which Stabilize Enzyme Activity

Several assays (See Examples 1–12) were used to determine the stabilizing or destabilizing actions of approximately 30 different anionic, cationic and amphoteric surfactants (summarized in Table 1). These experiments demonstrated that cationic surfactants can be utilized to stabilize enzyme activity. Cationic surfactants have found many applications including use as fungicides, as pesticides and as antiseptic agents in cosmetics. Cationic surfactants may be divided into two groups: 1) those containing nitrogen; and 2) non-nitrogen "onium" surfactants including phosphonium, sulfonium, sulfoxonium and arsonium surfactants. Nitrogen containing surfactants are easily and inexpensively prepared and far outnumber non-nitrogen surfactants. Nitrogen containing surfactants may be divided into two categories which differ in the nature of the nitrogen containing group. The first category comprises the alkyl nitrogen compounds such as simple ammonium salts containing a long-chain alkyl group which confers hydrophobicity and one or more amine hydrogens. The alkyl nitrogen compounds may also be secondary, tertiary, or quaternary ammonium compounds in which all amine hydrogens have been replaced by organic radical substitutions. For secondary, tertiary and quaternary amines, the substituted radical may be either long- or short-chain alkyls, alkylarlys, aryls or ethoxyls. The second category of nitrogen containing surfactants includes heterocyclic materials such as pyridinium, morpholinium and imidazolinium derivatives.

TABLE 1

Ionic Surfactants Tested in Enzyme Stabilization Applications

| ZWITTERIONIC DETERGENTS | Enzyme Stabilization |
|---|---|
| Ammonium Propanesulfonates | |
| N-dodecyl-n,n'-dimethyl-3-ammonio-1-propanesulfonate (Sigma Chem. Co. D4516, Lot 95H50545) | – |
| N-octadecyl-n,n-dimethyl-3-ammionio-1-propane-sulfonate (Sigma Chem. Co. O-8004, Lot 44H5006) | – |
| N-decyl-n,n-dimethyl-3-ammonium-1-propanesulfonate (Sigma D-4266, Lot 26H5029) | ± |
| N-tetradecyl-n,n-dimethyl-3-ammonio-1-propanesulfonate (Sigma Chem. Co. T-7763, Lot 96H5001) | – |
| Cholamino Derivatives | |
| Chaps (Sigma Chem. Co. C-3023, Lot 86H5022) | ± |
| Chapso (Sigma Chem. Co. C-3649, Lot 35H5065) | ± |
| Betaine Derivatives | |
| Mirataine CB (Rhone-Poulenc, North American Chemicals, Cranbury, NJ) | – |
| Mirataine BB (Rhone-Poulenc, North American Chemicals, Cranbury, NJ) | – |
| Mirataine CBR (Rhone-Poulenc, North American Chemicals, Cranbury, NJ) | – |
| Mirataine ACS (Rhone-Poulenc, North American Chemicals, Cranbury, NJ) | – |
| Other Zwitterionic Salts | |
| Miracare 2MHT (Rhone-Pouleric, North American Chemicals, Cranbury, NJ) | – |
| Miracare 2MCA (Rhone-Poulenc, North American Chemicals, Cranbury, NJ) | – |
| CATIONIC DETERGENTS | |
| Ethyoxylated Amines | |
| Tomah E-14-2 (Tomah Prod. Inc., Milton, WI) | – |
| Tomah E-14-5 (Tomah Prod. Inc., Milton, WI) | – |
| Tomah E-18-15 (Tomah Prod. Inc., Milton, WI) | + + + |
| Tomah E-18-5 (Tomah Prod. Inc., Milton, WI) | + + + |
| Modified Pyridines | |
| Cetylpyridinium chloride (Sigma Chem. Co. C-9002, Lot 77H1047 | – |
| Alkyl Ammonium Salts | |
| Tetradecyl-trimethyl-ammonium bromide (Sigma Chem. Co. T4762) | – |
| Dimethyl dioctadecyl Ammonium bromide (Sigma Chemical Co. D2779, Lot 105H1131) | – |
| ANIONIC DETERGENTS | |
| Cholic Acid-Like Surfactants | |
| Cholic acid (Sigma Chem. Co. C-1254 Lot 56H0339) | – |
| Taurocholic Acid (Sigma Chem. Co. T-4009, Lot 15H5001) | – |
| Polyoxyethylene Ethers | |
| TRITON X-200 (Sigma Chem. Co. X-200, Lot 75H0989) | – |
| TRITON W-30 (Sigma Chem. Co. W-30, Lot 18F0766) | – |
| TRITON X-301 (Sigma Chem. Co. 301, Lot 13H7706) | – |
| TRITON 770 (Sigma Chem. Co. 770, Lot 18F0768) | – |
| Other | |
| Dioctyl sulfosuccinate (Sigma Chem. Co. D4422) | – |

Accordingly, in some embodiments, the present invention provides cationic surfactants that stabilize enzyme activity. In preferred embodiments, the cationic surfactant preferably has a Hydrophile-Lipophile Balance (HLB) index number from about 10 to 17, most preferably from about 11 to 16.

The HLB index number is an index for correlating the chemical structure of surfactant molecules with their surface activity. The HLB index number may be calculated by a variety of empirical formulas (See e.g., Meyers, *Surfactant Science and Technology,* VCH Publishers Inc., New York, pp. 231–245 [1992]), incorporated herein by reference). The HLB index number ranges from 0 to about 70 or more for commercial surfactants. Hydrophilic surfactants are at the high end of the scale due to their high solubility in water and solubilizing properties, while surfactants with low solubility in water which are good solubilizers of water in oils are at the lower end of the scale.

In some embodiments of the present invention, the cationic surfactants are preferably ethoxylated amines. Ethoxylated amines contain a hydrophobic alkyl side chain and one or more long-chain polyoxyethylene groupings. The aqueous solubility of ethoxylated amines is to a large degree dependent on the extent of alkoxylation and is not always caused by salt formation. Simple polyoxyethylated amines (POE amines) are prepared from long chain alkylamines by ethoxylation. Most ethoxylated amines are water soluble and relatively weak bases. Ethyloxylated amines are mainly used as emulsifying and hair conditioning agents.

The cationic surfactant is preferably selected from the group of ethoxylated alkyl amines having the following general structure in aqueous solution:

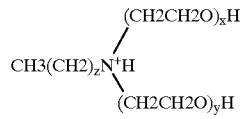

wherein z is an integer from about 15 to 20 and wherein x and y are each at least one and x+y has an average value of about 5 to 15 so that the HLB index number is from about 10 to 17, preferably from about 11 to 16. The nitrogen atom may be replaced by a sulphur atom to form an ethoxylated alkyl sulphide, a phosphorous atom to form an ethoxylated alkyl phosphine, or an arsenic atom to form an ethoxylated alkyl arsenine.

Most preferably, the cationic surfactant is selected from the group having the structures in aqueous solution:

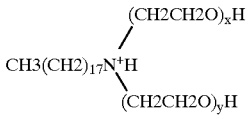

wherein x+y has an average value of 5 and:

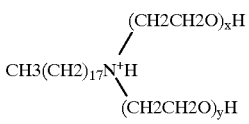

wherein x+y has an average value of 15.

B. Use of Cationic Surfactants in Storage and Reaction Buffers

The cationic surfactants described above may be used to stabilize enzymes in both storage buffers and in reaction buffers. These surfactants are useful for stabilization of various enzymes including, but not limited to, Taq polymerase, Tth polymerase, Tfl polymerase, MMLV Reverse Transcriptase, AMV reverse transcriptase, and T4 DNA polymerase. In some embodiments, the enzymes may be produced recombinantly or purified from the native organisms as is known in the art. In other embodiments, the enzymes may be purified in the absence of surfactants by column chromatography, or if purified in the presence of surfactants other than the cationic surfactants of the present invention, those surfactants may be removed by chromatography (See e.g., M. P. Deutscher (ed.), *Methods in Enzymology-Guide to Protein Purification,* Academic Press Limited, London [1990]).

In some embodiments of the present invention, storage buffers for thermostable and other enzymes comprise a buffering reagent in a concentration of about 10 to 70 mM (preferably about 50 mM Tris-HCl at pH 8.0), a salt in a concentration of about 50 to 150 mM (preferably about 100 mM KCl or NaCl), a chelator in molar ratio to the salt of about 1:500 to 1:1,500 (preferably about 0.1 mM EDTA), a reducing agent in a concentration of about 1 to 10 mM (preferably about 1 mM DTT (dithiothreitol)), glycerol in a concentration of about 50% by volume, and the cationic surfactant of the present invention in concentration of about 0.001% to 1.0% (preferably about 0.1%).

In other embodiments of the present invention, reaction buffers for thermostable polymerases and other enzymes comprise a buffering reagent in a concentration of about 5 to 15 mM (preferably about 10 mM Tris-HCl at a pH of about 8.0 to 9.0 at 25° C.), a monovalent salt in a concentration of about 20 to 100 mM (preferably about 50 mM NaCl or KCl), a divalent cation in a concentration of about 1.0 to 10.0 mM (preferably MgCl$_2$), dNTPs in a concentration of about 0.05 to 1.0 mM each (preferably about 0.2 mM each), and the cationic surfactant of the present invention in a concentration of about 0.001 to 1.0% by volume (preferably about 0.1%).

In still further embodiments of the present invention reaction buffers for thermolabile DNA polymerases, such as T4 DNA polymerase, comprise a buffering reagent in a concentration of about 5 to 15 mM (preferably about 10 mM Tris-HCl at pH 8.0), a monovalent salt at a concentration of about 30 to 70 mM (preferably about 50 mM NaCl), a divalent cation at a concentration of about 5 to 15 mM (preferably about 10 mM MgCl$_2$), a reducing agent at a concentration of about 0.5 to 5 mM (preferably about 1 mM DTT), and a cationic surfactant in a concentration of about 0.001% to 0.1% by volume (preferably about 0.01%).

In still other embodiments of the present invention, reaction buffers for reverse transcriptases such as MMLV reverse transcriptase comprise a buffering reagent in a concentration of about 30 to 70 mM (preferably about 50 mM Tris-Cl at a pH of about 8.3), a divalent cation at a concentration of about 5 to 15 mM (preferably MgCl$_2$ at about 7 mM), a monovalent salt at a concentration of about 20 to 60 mM (preferably KCl at about 40 mM), a reducing agent at a concentration of about 1 to 20 mM (preferably DTT at about 10 mM), and a cationic surfactant at a concentration of about 0.01 to 1.0% by volume (preferably at about 0.01% by volume).

Many equivalents exist for the components of the reaction and storage buffers described above and substitutions can readily be made. Therefore, these preferred buffers are intended only to serve as a guide for the preparation of buffers in which enzymes and polymerases may stored in and for buffers for carrying out polymerization and other enzyme reactions, and are not intended to limit the present invention. Indeed, it is not intended that the present invention be limited to stabilization of polymerases, as the present invention is suitable for the stabilization of proteins in general.

EXPERIMENTAL

The following examples are provided in order to demonstrate and further illustrate certain preferred embodiments and aspects of the present invention and are not to be read as limiting the scope thereof.

In the experimental disclosure which follows, the following abbreviations apply: ° C. (degrees Centigrade); bp (base pair); kb (kilobase pair); kD (kilodaltons); gm (grams); μg (micrograms); mg (milligrams); ng (nanograms); μl (microliters); μCi (microcurie); M (molar); mM (millimolar); μM (micromolar); nM (nanomolar); U (units); MW (molecular weight); sec (seconds); min(s) (minute/minutes); hr(s) (hour/hours); ab (antibody); HCl (hydrochloric acid); MgCl$_2$ (magnesium chloride); KCl (potassium chloride); NaCl (sodium chloride); PBS (phosphate buffered saline [150 mM NaCl, 10 mM sodium phosphate buffer, pH 7.2]); SDS (sodium dodecyl sulfate); Tris (tris(hydroxymethyl)aminomethane); EDTA (Ethylenediaminetetraacetic Acid); EGTA (Ethylene glycol-bis(B-amino-ethyl ether) N,N,N',N'-tetraacetic Acid); HEPES (4-(2-Hydroxyyethyl)piperazine-1-ethanesulphonic acid; w/v (weight to volume); v/v (volume to volume); Sigma (Sigma Chemical Co., St. Louis, Mo.), MMLV (Moloney Murine Leukemia Virus); AMV (Avian Myeloblastosis Virus); RT (Reverse Transcriptase); Taq (*Thermus aquaticus*); Tfl (*Thermus flavus*); Tth (*Thermus thermophilus*).

EXAMPLE 1

Ability of Taq Polymerase to Amplify a DNA Segment in the Presence or Absence of Detergent This Example describes the development of a PCR based assay for polymerase stabilization by detergents (i.e., surfactants). Conditions were defined in which the polymerase was incapable of producing a detectable amplification product in the absence of detergent, but could produce detectable amplification in the presence of a stabilizing detergent, such as Tween 20.

The following reaction mixture was assembled:
2 mM dNTP Mix 100 μl
2 ng/μl pGEM 1 uc 10 μl
Primer A (1 μg/μl) 10 μl
Primer B (1 μg/μl) 10 μl
10 X Taq buffer 100 μl
25 mM MgCl$_2$ 100 μl
Nanopure water 670 μl
Total 1000 μl pGEM 1 uc (Part # E1541) and 25 mM MgCl$_2$ (Part # M1902) were obtained from Promega Corp, Madison Wis. The 10× Taq buffer formulation was: 500 mM KCl, 100 mM Tris-Cl (pH 9.0 at 25° C.). The 10× Taq buffer was made by dissolving KCl and Trizma in nanopure water and adjusting the pH with concentrated hydrochloric acid. Nanopure water was made by autoclaving deionized water treated by a NANOPURE water system. The 2 mM dNTP mix was made by mixing 100 mM stocks of dATP, dCTP, dGTP, and dTTP (Promega U120, U122, U121 and U123, respectively) with nanopure water to produce a solution containing a 2 mM concentration of each nucleotide. The DNA sequences of the primers used were TAATACGACTCACTATAGGGCGAAT (SEQ ID NO: 1) and GAATCGTCGTATGCATG-TAAAACTC (SEQ ID NO 2).

One hundred microliters of the reaction mixture were placed into a 0.2 ml tube and 50 μl placed in five additional tubes. Another reaction mixture was assembled using the formulation described above except that 10 μl of 10% (v/v) Tween 20 (Sigma, P-1379) was used to replace 10 μl of the 670 μl of water. This reaction mixture had a final detergent concentration of 0.1% v/v Tween 20. This second reaction mixture was then dispensed so that one tube contained 100 μl of reaction mix and five additional tubes contained 50 μl of mix.

One microliter of Taq polymerase (10 U/μl), purified without the addition of any detergent in any step, was added to the detergent-containing and detergent-free reaction mixes and the contents of the tubes were mixed. Serial dilutions of detergent-containing and detergent-free reactions were made as follows. Fifty microliters of the first mixture was removed and added to the 50 μl of the same reaction mix in one of the five remaining tubes of reaction mix. This tube was mixed and 50 μl of the resulting mixture transferred to the next tube with 50 μl of reaction mix. The mixing and transfers were performed until all of the five tubes containing reaction mix were mixed with reaction mix containing enzyme. The tubes were placed in a thermocycler and put through the following program.

Pre cycling conditions: Adjust temperature to 94° C. for 1 min then proceed to cycling conditions.

Cycling conditions: For each cycle: adjust temperature to 94° C. for 15 sec, then lower temperature to 65° C. for 2 min. Repeat temperature cycling for 25 cycles. Proceed to post cycling conditions.

Post cycling conditions: Adjust temperature to 68° C. for 4 min then lower temperature to 4° C.

After the tubes were cycled through the program conditions listed above, 5 μl of Stop Solution was added to each tube. Stop solution was: 0.4% SDS, 160 mM EDTA, 0.16% Orange G and 24% glycerol.

The reaction products were analyzed by agarose gel electrophoresis. Agarose (3 g) was added to a flask containing 300 ml of 1× TBE buffer. The solution was boiled by microwave heating and the contents of the flask were swirled. Thirty microliters of a solution of 10 mg/ml of ethidium bromide were then added and molten agarose was poured into a gel cassette with a comb for a BRL Model H4 Horizontal Gel Electrophoresis System and allowed to harden. After hardening, the comb was removed and the gel cassette was placed into the bed of the electrophoresis system that had previously been filled with 1× TBE buffer. Twenty-five microliter samples of each of the amplification reactions along with a sample of pGEM marker were loaded into individual wells in the gel. Electrophoresis was performed at 100 V for 2 hr using a Hoffer PS500X DC Power Supply, then the gel was visualized under U.V. light using an Ambis system.

A strong band of 1.5 kb DNA was seen in the lane containing the sample from the amplification reaction which had the highest amount of Taq polymerase and 0.1% Tween 20. Weaker 1.5 kb bands were seen in the lanes containing the amplification reaction with the second highest level of Taq polymerase and 0.1% Tween 20, and the 1.5 kb band was not seen in the lane containing the highest level of Taq polymerase without added detergent.

Thus, these conditions are useful to test the ability of detergents to stabilize Taq polymerase during amplification reactions. Materials that stabilize the enzyme increase the strength of the 1.5 kb DNA band produced in the reaction above what is produced in reactions without detergent. Exceptionally good stabilizing materials are identified as those that allow production of the 1.5 kb DNA band at enzyme concentrations lower than those observed using 0.1% Tween 20.

EXAMPLE 2

Screening of Surfactants

In this example, surfactants were screened for their ability to stabilize enzymes. The following compounds were dissolved in nanopure water to a final concentration of 10% (either w/v or v/v depending if the material was a solid or liquid, respectively): Tetradecyl-trimethyl-ammonium bromide (Sigma T4762), Dioctyl sulfosuccinate (Sigma D-4422), Cholic Acid (Sigma C-1254 lot 56H0339), Taurocholic Acid (Sigma T-4009, lot 15H5001), Chaps (Sigma C-3023, lot 86H5022), Chapso (Sigma C-3649, lot 35H5065), Cetylpyridinium chloride (Sigma C-9002, lot 77H1047), Tween 20 (Sigma P-1379) and TRITON X-100.

A 10× buffer was made with each of these surfactant solutions. The 10× buffer for each consisted of: 500 mM KCl, 100 mM Tris-HCl pH 9.0 (at 25° C.), 1% surfactant (made by a 1:10 dilution of the detergent solution described above into the buffer during formulation). As described in Example 1, the Taq polymerase used in these experiments was purified without exposure to any detergents. Each of these buffer solutions was used to formulate a Taq-surfactant solution as follows:

| | |
|---|---|
| Nanopure water | 255 μl |
| 10X surfactant buffer | 32 μl |
| 25 mM MgCl$_2$ | 32 μl |
| Taq polymerase (10 U/μl) | 1 μl |
| Total volume | 320 μl |

A control solution was made as indicated above, except that the 32 μl of 10× buffer without surfactant was used. The solutions were incubated at 95° C. and samples (10 μl) were removed and placed in a fresh tube, and kept on ice at 0, 5, 10, 30, 60, 90, and 120 min. The samples were then assayed for Taq polymerase activity.

Taq polymerase activity was determined by measuring the amount of tritiated deoxynucleotide base a sample of the enzyme could incorporate. The assay was performed as follows. Solutions of dATP, dCTP, dGTP and dTTP (Promega U120, U122, U121 and U123, respectively) were diluted to 2 mM final concentration (originally at 100 mM) using nanopure water. Tritiated nucleotide $^3$H-TTP was obtained from Amersham (TRK424, 250 μCi/250 μl). The template for incorporation was calf thymus DNA (Sigma, D-1501) dissolved in 10 mM Tris-HCl pH 7.3, 5 mM MgCl$_2$ to a final concentration of 2.5 mg/ml. Prior to use, the DNA was treated with 1 μl of a 1:10 dilution of RQ1 DNAse (Promega M610) (dilution made using 10 mM Tris-HCl, 5 mM MgCl$_2$) and incubated for 10 min at 37° C. followed by 30 min at 68° C. This was done to "activate" the DNA for incorporation. A 10× Taq assay buffer was made containing 500 mM Tris-HCl (pH 9.0 at 25° C.), 500 mM NaCl, and 100 mM MgCl$_2$.

The following reaction mix was assembled:

| | |
|---|---|
| 10X Taq Assay Buffer | 500 μl |
| Nanopure water | 1700 μl |
| dATP (2 mM) | 500 μl |
| dCTP (2 mM) | 500 μl |
| dGTP (2 mM) | 500 μl |
| dTTP (2 mM) | 500 μl |

| | |
|---|---|
| Activated calf thymus DNA | 600 µl |
| ³H-TTP(1 µCi/ul) | 100 µl |

Time point samples (10 µl) were added to 40 µl of the reaction mix and then incubated at 74° C. for 10 min. After incubation, the solution was diluted with 500 µl of ice cold 10% TCA. The TCA solution was filtered through a GF/A filter. The tube was washed three times with 1 ml of 5% TCA and the wash was then filtered onto the same filter. The filter was then rinsed 3 times with 5% TCA and then rinsed with acetone. The filters were dried 10 min. with a heat lamp and then the radioactivity was counted. The percent of activity present at any time point was determined by dividing the net counts for the sample at that time point by the net counts of the 0 min sample for that enzyme solution and then multiplying by 100%. The percent activity of the solution was plotted versus time. The points were then connected by a smooth curve and the estimated half-life of the enzyme under the conditions chosen was estimated based on the point where the line crossed 50% activity.

The percent of activity remaining at the different times was then determined and plotted to estimate the half life of the enzyme in the presence of these surfactants. The results indicated that the ionic surfactant solutions containing Chaps and Chapso had estimated half lives of approximately 5 min. The non-ionic surfactant solutions containing Tween 20 and TRITON X-100 had half-lives of approximately 40 min. The control solution without surfactant had a half-life of less than 5 min. All the other ionic surfactant solutions had half-lives less than 5 min.

Thus, this assay is useful for identifying ionic surfactants that provide some degree of stabilization to Taq polymerase, as seen with Chaps and Chapso. In addition, this assay can be used to identify ionic surfactants that greatly stabilize Taq polymerase. Such surfactants increase the half life of Taq polymerase under these conditions to a value about equal to or greater than seen with Tween 20.

EXAMPLE 3

Screening of Additional Surfactants

In this example, additional surfactants were screened for the ability to stabilize proteins. Solutions (10% w/v or v/v) of the following materials were made in nanopure water: N-dodecyl-n,n'-dimethyl -3-ammonio-1-propanesulfonate (Sigma D-4516, lot 95H5045), Mega 10 (Sigma D-6277, lot 37H5041), N-octadecyl-N,N-dimethyl-3-ammionio-1-propane-sulfonate (Sigma O-8004, lot 44H5006), SB 3-10, N-Tetradecyl-N,N-dimethyl-3 Ammonio-1-propanesulfonate (Sigma T-7763, lot 96H5001), Dimethyl dioctadecyl Ammonium bromide, TRITON X-200 (Sigma X200, lot 75H0989), TRITON W-30 (Sigma Chem Co., W-30, lot 18F0766), TRITON X-301 (Sigma X301, lot 13H7706), TRITON 770 (Sigma 770, lot 18F0768).

Ninety-nine microliter aliquots of the master reaction mix described in Example 1 were placed into separate 0.2 ml tubes, then 1 µl of the 10% surfactant solutions and 2 µl of Taq polymerase (10 U/µl) purified in the absence of detergent were added to each tube. Control reactions consisted of tubes containing 1 µl of 10% Tween 20 (positive control) and no surfactant (negative control). The tubes were subjected to the amplification conditions and gel analysis protocol as in Example 1 above.

A strong 1.5 kb DNA band was produced in the Tween 20 supplemented reaction, and a weaker but visible band was produced in the reaction without added surfactant. All other reactions failed to produce a visible 1.5 kb DNA fragment, except the reaction supplemented with N-decyl-N, N-dimethyl-3-ammonium-1-propane sulfonate. This reaction produced a band intermediate in intensity between that seen for the no detergent reaction (negative control) and the reaction supplemented with Tween 20.

A second set of reactions was assembled where 95 µl of the master reaction mix was placed into tubes with 5 µl of the surfactant solutions and 2 µl of Taq polymerase (10 U/µl). Tween 20 and no surfactant controls were also assembled. Reactions were conducted according to the amplification conditions and analyzed by gel electrophoresis as described above.

A strong 1.5 Kb DNA band was seen in the Tween 20 supplemented reaction and no band was seen in the reaction without added surfactant. All other reactions failed to produce a visible 1.5 kb DNA fragment, even the reaction supplemented with N-decyl-N, N-dimethyl-3-ammonium-1-propase sulfonate. These results indicate that none of these surfactants is equivalent to Tween 20 as a stabilizing agent for Taq polymerase.

EXAMPLE 4

Screening of Additional Surfactants

In this example, additional surfactants were screened for the ability to stabilize proteins. Solutions (10% w/v or v/v) of the following materials were made in nanopure water: Miracare ZMHT, Miracare ZMCA, Mirataine BB, Mirataine ACS, Mirataine CBR, and Mirataine CB (Rhone-Poulenc, North American Chemicals, Cranbury, N.J.). The surfactant solutions were tested at the 0.1% level as described in Example 3 by comparison with Tween 20 and no surfactant control reactions, except that the enzyme concentration was lowered to 10 U of Taq per 100 µl reaction mix.

A strong 1.5 kb DNA band was seen in the Tween 20-supplemented reaction and no band was seen in the reaction without added surfactant. All of the other reactions failed to produce a visible 1.5 kb DNA fragment. These results indicate that none of these surfactants is equivalent to Tween 20 as a stabilizing agent for Taq polymerase.

EXAMPLE 5

Initial Evaluation of Surfactants From Tomah

In this example, the ability of ethoxylated amines to stabilize proteins was examined. Solutions (10% w/v or v/v) of the following materials were made in nanopure water: Tomah E-14-2, Tomah E-14-5, Tomah E-18-15, and Tomah E-18-5 (Tomah Prod. Inc., Milton, Wis.). The surfactant solutions were tested at the 0.1% level and evaluated as in example 3 above by comparison with Tween 20 control reactions, except that the enzyme concentration was lowered to 10 U of Taq per 100 µl reaction mix.

A strong 1.5 Kb DNA band was produced in the Tween 20, Tomah E-18-15 and Tomah E-18-5 supplemented reactions. The reactions supplemented with Tomah E- 14-2 and Tomah E-14-5 failed to produce a visible 1.5 kb DNA fragment. These results indicate that Tomah E-18-15 and Tomah E-18-5 stabilize Taq polymerase, and that Tomah E-14-2 and Tomah E-14-5 do not. In addition, the Tomah E-18-5 and Tomah E-18-15 appeared to stabilize the enzyme about as effectively as Tween 20. Thus, further tests were conducted with these surfactants.

All the Tomah detergents are given the chemical description of ethoxylated amines, and are cationic detergents. However, they differ in their HLB index number as reported in McCutcheon's Volume 1: Emulsifiers and Detergents North American Edition, 1996. The HLB values for these materials and some nonionic detergents that stabilize Taq polymerase are given in Table 2. These results suggest that cationic detergents with HLB indices in the 11–16 range are effective in stabilizing Taq polymerase.

TABLE 2

| Detergents | HLB Index |
| --- | --- |
| Tomah E-14-2 | 8.3 |
| Tomah E-15-5 | 5.0 |
| Tomah E-18-5 | 11.0 |
| Tomah E-18-15 | 16.0 |
| TRITON X-100 | 13.5 |
| Tween 20 | 16.7 |

EXAMPLE 6

Further Testing of Ethoxylated Amines

The initial results seen with the Tomah E-18 surfactants suggested that these materials might stabilize Taq polymerase at least as well as nonionic detergents. In order to obtain a more precise idea of how these materials work, experiments were performed with lower levels of enzyme and detergent.

Reaction mixes were assembled containing 0.1%, 0.01% and 0.001% Tween 20, Tomah E-18-15 and Tomah E-18-5 as described in Example 3 above. Detergent-free Taq polymerase was added to these mixes to form reactions containing 10, 5, 2.5 and 1.25 U of Taq polymerase per reaction. The reactions were incubated in a thermocycler and the reaction products analyzed as described in Example 1 above.

Almost all lanes contained the expected 1.5 kb DNA fragment. In most cases, it was difficult to determine whether any lanes with one detergent had a stronger band than the other detergents. However, when low levels of enzyme and/or detergent were present, the reactions containing the ionic detergents appeared to produce more product than did the reactions containing the nonionic detergent.

EXAMPLE 7

Improved Half-Life of Taq Polymerase Under High Temperature Incubation Conditions in the Presence of Ionic Detergents In this example, the ability of ethoxylated amines to stabilize thermostable proteins at high temperatures was examined. Solutions of detergent-free Taq polymerase (2.5 U/100 $\mu$l of solution) containing 0.005% Tomah E-18-15, Tomah E-18-5, Tween 20, NP-40, and TRITON X-100 were produced as in Example 2. These solutions were incubated at 95° C. and samples were removed at 0, 10, 30, 60 and 120 min and analyzed as in Example 2. The half lives of the enzyme in the presence of these surfactants was estimated graphically. The solutions containing Tomah E-18-5, TRITON X-100 and NP-40 all had Taq polymerase half lives of about 8 min. The solution containing Tween 20 had a 50 min. half life and the solution containing Tomah E-18-15 had an estimated half life of 70 min. These results indicate that these two cationic surfactants stabilize Taq polymerase under high temperature conditions as well as or better than the nonionic surfactants normally used to stabilize the enzyme.

EXAMPLE 8

Use of Ionic Detergents for Improvement of the Performance of Tth Polymerase

After determining that Tomah E-18-5 and Tomah E-18-15 improved the performance of Taq polymerase, additional experiments were performed to determine if this effect could be demonstrated with other enzymes. In this experiment, the stabilization of the thermostable Tth polymerase in the presence of cationic and nonionic surfactants was examined. Triplicate 10 ml samples of the following solutions were assembled:

| | |
| --- | --- |
| 2M Tris-HCl pH 7.5 | 50 $\mu$l |
| 3M KCl | 1 ml |
| 1M DTT | 10 $\mu$l |
| 0.5M EDTA, pH 8.0 | 2 ml |
| Bovine Serum Albumin (10 mg/ml) | 500 $\mu$l |
| Glycerol | 5 ml |
| Surfactant stock | 2 ml |
| Nanopure water | to 10 ml |

Solution A contained 2 ml of a 10% stock of TRITON X-100; solution B contained 1 ml of a 10% stock of Tween 20 and 1 ml of a 10% stock of NP40; solution C contained 2 ml of a 10% stock of Tomah E-18-15. A sample of Tth polymerase (Promega M210, lot 8502201) was mixed in equal volume with each of these solutions to produce three enzyme detergent solutions containing 2.5 U/$\mu$l of Tth polymerase. A reaction mix was assembled as described using the materials in Example 1, except that a new 10× Buffer was used. This buffer was made by mixing 1.67 ml of 3M KCL, 0.5 ml of 2M Tris-HCl pH 8.3 (25° C.) and 7.83 ml of nanopure water. Four microliters of each enzyme detergent solution was then added to 200 $\mu$l of the reaction mix and mixed. One hundred microliters of this solution was then removed, mixed with another 100 $\mu$l of reaction mix and a second 100 $\mu$l of the mix removed. This mix was then added to a second 100 $\mu$l of reaction mix and mixed. This process was continued until 6 tubes were produced that contained reaction mix and 5, 2.5, 1.25, 0.625, and 0.3125, and 0.156 units of Tth polymerase. Thermocycling was performed as described in Example 1. The products of the reaction were then analyzed as described in Example 1.

A clear 1.5 kb band was present in the lanes that were fractionated from TRITON X-100 stabilized enzyme having 5, 2.5 and 1.25 unit of enzyme. A clear 1.5 kb band was present in the lanes that were used to analyze the Tween 20 and NP40 stabilized enzyme having 5, 2.5, 1.25 and 0.625 units of enzyme. A clear 1.5 kb band was present in the all lanes used to analyze the Tomah E- 18-15 stabilized enzyme reactions except for the 0.156 unit reaction.

These results indicate that the ionic detergent Tomah E-18-15 improves the performance of Tth polymerase and that the level of improvement is greater than that seen with the nonionic detergents used in this study. This is particularly interesting in that this enzyme is both a reverse transcriptase as well as a DNA polymerase, thus indicating that the detergents of the present invention are useful in stabilizing both of these types of enzymes.

EXAMPLE 9

Improved Performance of T4 DNA Polymerase Using Ionic Detergents

Since Tomah E-18-15 improved the performance of two different thermostable DNA polymerases, one with reverse transcriptase activity, its effect on the activity of a non-thermostable DNA polymerase (i.e., T4 DNA polymerase) was tested.

The following solution was prepared:

| | |
|---|---|
| Nanopure water | 960 µl |
| 10X Buffer* | 200 µl |
| 2 mM dNTP mix | 200 µl |
| Activated DNA | 200 µl |
| $^3$H-TTP (1 µCi/µl) | 40 µl |

*The 10X buffer in this example contained 1 ml of 5M NaCl, 0.5 ml of 2M Tris-HCl pH 8.0 (25° C.), 1 ml of 1M MgCl$_2$, 100 µl of 1M DTT adjusted to a final volume of 10 ml with the addition of nanopure water. The 2 mM dNTP mix was made as per Example 1.

Example 1.

T4 DNA Polymerase (Promega M421) was diluted 1:100 into the 1× buffer. The reactions were assembled on ice as presented in Table 3.

TABLE 3

| | Reaction Number | | | | | |
|---|---|---|---|---|---|---|
| Components | 1 & 2 | 3 & 4 | 5 | 6 | 7 | 8 |
| 0.1% Tomah E-18-15 | 0 | 0 | 0.5 | 5 | 0 | 0 |
| 1% Tomah E-15-18 | 0 | 0 | 0 | 0 | 2.5 | 5 |
| Nanopure water | 10 | 5 | 4.5 | 0 | 2.5 | 0 |
| Diluted T4 DNA polymerase | 0 | 5 | 5 | 5 | 5 | 5 |
| Reaction mix | 40 | 40 | 40 | 40 | 40 | 40 |

The tubes were incubated at 37° C. for 15 min, and the amount of TCA precipitable counts were measured to determine the activity of the enzyme at these surfactant levels. The data is presented in Table 4. These results indicate that this enzyme is about 79% and 68% more active in the presence of 0.001% and 0.01% surfactant, respectively.

TABLE 4

| Reaction | Counts/min |
|---|---|
| 1 | 136 |
| 2 | 202 |
| 3 | 4568 |
| 4 | 4916 |
| 5 | 8358 |
| 6 | 7864 |
| 7 | 5106 |
| 8 | 4720 |

In order to confirm these findings, and to determine if the surfactant can increase the activity of this enzyme in the presence of BSA, the following experiment was performed. Two reaction mixes were assembled as described above, except that the 10× reaction buffer for one of the mixes (i.e., the +BSA mix) was made using 1.7 ml of 10 mg/ml BSA with a corresponding decrease in the amount of nanopure water used to adjust the volume of the component solution to 10 ml. Two sets of reactions were assembled on ice as presented in Table 5.

TABLE 5

| | Reaction Number | | |
|---|---|---|---|
| Component | 1 & 2 | 3, 4, & 5 | 6, 7, and 8 |
| 0.1% Tomah E-18-15 (µl) | 0 | 0 | 5 |
| Nanopure water (µl) | 10 | 5 | 0 |

TABLE 5-continued

| | Reaction Number | | |
|---|---|---|---|
| Component | 1 & 2 | 3, 4, & 5 | 6, 7, and 8 |
| T4 DNA polymerase (µl) | 0 | 5 | 5 |
| Reaction mix (µl) | 40 | 40 | 40 |

*The T4 DNA polymerase was again diluted 1:100 with 1X buffer as above.
**One reaction mix was used for each set of tubes, thus one set contained BSA and the other set did not.

The tubes were incubated 15 min. at 37° C. and the amount of TCA precipitable counts measured to determine the activity of the enzyme in these solutions. The data are presented in Table 6. These results indicate that: 1) the ionic detergent improves the activity of this thermolabile polymerase; 2) the activity increase is similar to that seen with the addition of BSA, a material known to help the enzyme maintain its activity upon dilution; 3) the activity increase seen with the surfactant is slightly greater than seen with BSA separately; and 4) the activity of the enzyme in the presence of both of these materials is slightly higher than seen upon the addition of BSA alone.

TABLE 6

| Reaction Number | Counts/min (−BSA Reactions) | Counts/min (+BSA Reactions) |
|---|---|---|
| 1 | 210 | 434 |
| 2 | 154 | 420 |
| 3 | 4124 | 6338 |
| 4 | 4488 | 6332 |
| 5 | 4502 | 6328 |
| 6 | 6762 | 6678 |
| 7 | 6500 | 6100 |
| 8 | 6894 | 7752 |

EXAMPLE 10

Improved Performance of MMLV Reverse Transcriptase Upon the Addition of Ionic Detergent Since the ionic detergent Tomah E-18-15 improved the performance of a thermostable enzyme with reverse transcriptase activity (Tth polymerase), the effect of this surfactant on another reverse transcriptase, MMLV-RT, was examined.

10× MMLV-RT reaction buffer was prepared as follows:

| | |
|---|---|
| 2M Tris-HCl pH 8.3 (at 25° C.) | 2.5 ml |
| 1M MgCl$_2$ | 0.7 ml |
| 3M KCl | 1.33 ml |
| 1M DTT | 1 ml |
| Nanopure water | to a total volume of 10 ml |

An assay mix was made as follows:

| Component | Amount |
|---|---|
| 10X MMLV Reaction Buffer | 500 µl |
| Nanopure water | 3200 µl |
| 100 mM dTTP | 25 µl |
| Poly rA/Oligo dT* | 1250 µl |
| $^3$H-dTTP | 25 µl |

The PolyA/Oligo dT (Supertech, cat # 111020A) was 1 mM polyA, 0.1 mM Oligo dT. A sample of MMLV-RT (Promega M170, lot# 8157702) was diluted 1:100 with assay buffer. Reactions were assembled on ice as indicated in Table 7.

TABLE 7

|  | Reaction Number | | |
| --- | --- | --- | --- |
| Components | 1 & 2 | 3 & 4 | 5 & 6 |
| 0.25% Tomah E-18-15 (μl) | 0 | 0 | 2 |
| 1:100 diluted MMLV-RT | 0 | 2 | 2 |
| Assay Mix | 50 | 50 | 50 |

These reactions were incubated 10 min. at 37° C., 10 μl of 1 mg/ml calf thymus DNA and 0.5 ml of 10% TCA was added, and the tubes placed on ice for 10 min. The reactions were then filtered using GF/C filters and the filters were washed and counted. The data are presented in Table 8. These data indicate that the performance of this reverse transcriptase is increased when stabilized with the ionic detergent under the conditions given above.

TABLE 8

MMLV-RT Activity

| Reaction | Counts/min |
| --- | --- |
| 1 | 74 |
| 2 | 128 |
| 3 | 2836 |
| 4 | 2960 |
| 5 | 5056 |
| 6 | 4400 |

EXAMPLE 11

Improved Performance of AMV Reverse Transcriptase Upon Addition of Ionic Detergent.

Since the ionic detergent Tomah E-18-15 improved the performance of MMLV reverse transcriptase (Example 10), the effect of this surfactant on another reverse transcriptase, AMV-RT, was examined following the procedure detailed in Example 10. These data (see Table 9) indicate that the performance of AMV reverse transcriptase is increased when it is assayed with the ionic detergent under the conditions detailed in Example 10.

TABLE 9

Cationic Surfactant Improves AMV-RT Activity

| Reaction | Counts/Min Sample A | Counts/Min Sample B |
| --- | --- | --- |
| No surfactant/No AMV-RT | 34 | 56 |
| No surfactant/with AMV-RT | 1950 | 4444 |
| 0.01% Tomah E-18-15 and AMV-RT | 3386 | 9401 |
| Percent improvement in the presence of 0.01% Tomah E-18-15 | 75 | 112 |

EXAMPLE 12

Improved Performance of Tfl DNA Polymerase Upon Addition of Ionic Detergent

Solutions of detergent-free Tfl polymerase were tested in a PCR reaction in the presence of Tomah E-18-15 detergent. The first reaction contained 0.1% detergent and 5 units Tfl polymerase. A series of PCR reactions made up of a 1:2 dilution series of the first reaction, was generated down to a final reaction containing 0.003% detergent and 0.15 units of Tfl polymerase. A no-detergent control was also performed. The resulting PCR product was run on an agarose gel, stained with ethidium bromide, and visualized using UV light. The data are presented in Table 10. In the absence of any added detergent, the Tfl polymerase did not generate any visible PCR product after 25 cycles. In the presence of Tomah E-18-15, a PCR product was visibly detectable when using from 5 units to 0.039 units of Tfl in the presence of 0.1% to 0.0005% detergent.

TABLE 10

Improved Performance of Tfl Polymerase

| Reaction | Tomah E-18-15(%) | Tfl polymerase (units) | Band on gel |
| --- | --- | --- | --- |
| 1 | 0.1 | 5 | + |
| 2 | 0.05 | 2.5 | + |
| 3 | 0.025 | 1.25 | + |
| 4 | 0.0125 | 0.625 | + |
| 5 | 0.006 | 0.312 | + |
| 6 | 0.003 | 0.156 | + |
| 7 | 0.0015 | 0.078 | + |
| 8 | 0.0005 | 0.039 | + |
| 9 | 0.0003 | 0.020 | − |
| 10 | none | 5 | − |

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, biochemistry, protein chemistry, or related fields are intended to be within the scope of the following claims.

What is claimed is:

1. A composition comprising a) a polymerase; and b) a polyethoxylated amine.

2. The composition of claim 1, wherein said polyethoxylated amine has an HLB index number of about 11–16.

3. The composition of claim 1, wherein said polyethoxylated amine has the molecular structure:

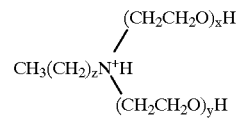

wherein z is an integer from about 15 to 20 and x+y has an average value of about 5 to 15.

4. The composition of claim 3 wherein z is 18 and x+y has an average value of 5.

5. The composition of claim 3 wherein z is 18 and x+y has an average value of 15.

6. The composition of claim 1, wherein said polyethoxylated amine is at a concentration of 0.0005 percent to 1.0 percent by volume.

7. The composition of claim 1, further comprising a buffer in a concentration about 10 mM to 70 mM.

8. The composition of claim 1 further comprising a salt selected from the group consisting of NaCl and KCl.

9. The composition of claim 1 further comprising a divalent salt selected from the group consisting of $MgCl_2$ and $CaCl_2$.

10. The composition of claim 1 further comprising a chelator.

11. The composition of claim 1 further comprising a reducing agent.

12. A composition consisting essentially of:
   a) a purified polymerase; and
   b) a polyethoxylated amine.

13. The composition of claim 12, wherein said polyethoxylated amine has the molecular structure:

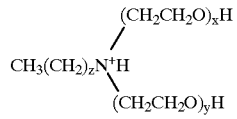

wherein z is an integer from about 15 to 20 and x+y has an average value of about 5 to 15.

14. The composition of claim 13 wherein z is 18 and x+y has an average value of 5.

15. The composition of claim 13 wherein z is 18 and x+y has an average value of 15.

16. The composition of claim 13 further comprising a chelator.

17. The composition of claim 12 wherein said polyethoxylated amine is at a concentration of 0.0005 percent to 1.0 percent by volume.

18. The composition of claim 12, wherein said polyethoxylated amine surfactant has an HLB index number of about 11–16.

19. A method comprising:
   a) providing a polymerase having activity and a polyethoxylated amine; and
   b) combining said polymerase and said polyethoxylated amine to form a mixture, under conditions such that said activity of said polymerase is stabilized.

20. The method of claim 19, wherein said polyethoxylated amine has an HLB index number of from about 10 to 17.

21. The method of claim 19, wherein said polyethoxylated amine has the molecular structure:

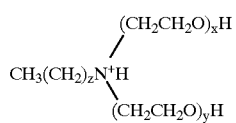

wherein z is an integer from about 15 to 20 and x+y has an average value of about 5 to 15.

22. The method of claim 21 wherein z is 18 and x+y has an average value of 5.

23. The method of claim 21 wherein z is 18 and x+y has an average value of 15.

* * * * *